United States Patent [19]

Allen

[11] 4,303,596

[45] Dec. 1, 1981

[54] SILICONE-CONTAINING ELASTOMER AND PROCESS FOR THE PREPARATION THEREOF

[75] Inventor: Dwight L. Allen, Akron, Ohio

[73] Assignee: Akron Catheter, Inc., Chippewa Lake, Ohio

[21] Appl. No.: 181,754

[22] Filed: Aug. 27, 1980

Related U.S. Application Data

[62] Division of Ser. No. 963,085, Nov. 22, 1978.

[51] Int. Cl.$^3$ .......................... C08K 5/54; C08K 3/22; C08L 7/02; C08K 3/34
[52] U.S. Cl. ................................ 260/746; 128/349 R; 260/29.1 SB; 260/29.7 NR; 260/42.56
[58] Field of Search ................ 260/3, 29.1 SB, 42.56, 260/746, 29.7 NR; 128/349 R, DIG. 9

[56] References Cited

U.S. PATENT DOCUMENTS

| | | | |
|---|---|---|---|
| 2,720,495 | 10/1955 | Phreaner | 260/42.15 |
| 3,962,519 | 6/1976 | Rüsch et al. | 260/37 SB |
| 3,969,289 | 7/1976 | Coffin et al. | 521/71 |
| 4,104,322 | 8/1978 | Snavely | 525/105 |

Primary Examiner—Wilbert J. Briggs, Sr.
Attorney, Agent, or Firm—Hamilton, Renner & Kenner

[57] ABSTRACT

A novel elastomeric composition of matter comprises a suitable elastomer, a masterbatch consisting of a silicone compound in an amount of from about 10 to about 50 parts by weight based upon the weight of the elastomer, titanium dioxide, and clay. A process for the preparation of a silicone-containing elastomeric composition of matter is provided and includes the steps of masterbatching a silicone compound, clay and titanium dioxide to form a dispersion, adding the dispersion to the elastomer and thereafter forming and curing a desired product therefrom. The composition is useful in the manufacture of rubber goods such as surgical and medical products which can be single or multi-layered.

5 Claims, No Drawings

SILICONE-CONTAINING ELASTOMER AND PROCESS FOR THE PREPARATION THEREOF

CROSS-REFERENCE TO RELATED APPLICATION

This application is a division of U.S. Ser. No. 963,085, filed Nov. 22, 1978.

TECHNICAL FIELD

The present invention relates to a novel elastomeric composition of matter, which contains a relatively high amount of a silicone compound, and a process for making the composition. The composition is particularly suitable for the manufacture of medical and surgical instruments such as endo-tracheal tubes, intraveneous tubing and specifically, Foley catheters, and it can easily be utilized in conventional multiple-dip manufacturing processes.

Catheters, as well as other medical and surgical instruments, have customarily been manufactured from natural latex primarily because the products have a low permeability, they are easily fabricated and are relatively inexpensive. The rubber composition selected must not only be susceptible to sterilization and other cleaning operations, but it must also be able to function satisfactorily when in contact with the body and its fluids. Whether the use is of a prolonged indwelling nature or short term and repeated, a catheter must remain impermeable to water and urine. Swelling of the rubber composition due to absorption of fluid, as well as deposition of various body materials are common disadvantages sought to be avoided.

Frequent attempts to improve the catheters have been made by varying the composition. Greater lubricity, for instance, can be achieved by utilization of silicone compounds which can result in less tissue irritation, resistance to the adhesion of calculi and longer service life.

Moreover, insertion and removal of catheters containing silicone is facilitated due to the smooth, oily-type surface thereof. It has been found that while pure silicone rubber possesses these desirable features, it often lacks sufficient strength to produce useful instruments. As a further disadvantage, the manufacture of such products via multiple dipping is not possible, requiring separate cementing of molded catheter tips and funnels to the drainage and inflation tubes. Incorporation of the silicone compound in the natural rubber latex blend imparts the advantages of the silicone to the latex and yet avoids the weaknesses inherent in the use of an all silicone rubber.

BACKGROUND ART

While it has been known to combine silicone emulsions with natural rubber latex in minute amounts, on the order of 0.025 parts by weight of the latex, for purposes of defoaming or reducing adhesion characteristics of the latex foam, combinations of larger amounts have not been successful inasmuch as they are merely mixtures of the components which tend to separate or "bleed-out" of the latex with migration to the surface. Such bleeding presents problems in the manufacture and use of multi-layered products such as de-lamination, local areas of surface tack and in the case of Foley catheters, weaknesses in the inflatable balloon.

Natural rubber latex compounds suitably employed for the manufacture of high quality surgical tubing and catheters comprise 96% rubber by weight and 4% of other ingredients such as curatives, fillers, anti-oxidants and stabilizers. These formulations have not heretofore accepted even small amounts of silicone, i.e., 3 to 5% by weight per hundred parts of rubber, and produced finished products having satisfactory functional characteristics.

One U.S. Pat. No. 3,962,519, does provide for incorporating silicone compounds in natural and synthetic rubber and relies upon the bleeding or migration of the silicone compound to the external surface of the instrument to provide resistance to unwanted adhesion and water repellency. The patent discloses employment of silicone compounds having a molecular weight of more than 90,000 and states that the amount present can range from about 0.1 to 10% by weight based upon the weight of the rubber. Of course, due to the migratory behavior of the silicone, incorporated according to the disclosure of this patent, relatively high amounts of silicone cannot be employed without causing separation of the silicone from the rubber latex and concommitant failure of the product. Notwithstanding the disclosure and claims of this prior patent, I have not found it possible to incorporate more than about 1% of a silicone compound of the type disclosed therein and form a satisfactory product.

DISCLOSURE OF THE INVENTION

It is therefore an object of the present invention to provide an elastomeric composition comprising from about 10 to about 50 percent by weight of a silicone compound, based upon the weight of the elastomer which composition is essentially free from deleterious phasing.

It is another object of the present invention to provide medical and surgical instruments from the novel elastomer disclosed herein which have greater water repellency, smoother surfaces, higher lubricity and longer life than existing instruments.

It is yet another object of the present invention to provide an elastomeric composition of natural rubber latex and a silicone compound the combination of which eliminates known disadvantages of the separate components without loss of the advantages thereof.

It is a further object of the present invention to provide a process for the preparation of an elastomeric composition comprising from about 10 to about 50 percent by weight of a silicone compound, based upon the weight of the elastomer.

It is still another object of the present invention to provide a process for the preparation of a silicone-containing elastomeric composition that is essentially free from deleterious phasing, allowing the manufacture of useful, long-lasting surgical and medical instruments therefrom via conventional processes.

It is yet another object of the present invention to provide surgical and medical instruments, such as Foley catheters, from the silicone-containing elastomeric compositions disclosed herein having from about 10 to about 50 percent of a silicone compound, based upon the weight of the elastomer.

These and other objects of the present invention, together with the advantages thereof over the prior art, which shall become apparent from the specification that follows, are accomplished by the invention as hereinafter described and claimed.

In general, the preferred elastomeric composition of the present invention comprises a rubber latex and from about 20 to about 85 parts by weight of a masterbatch which includes, based upon the weight of the elastomer, from about 10 to about 50 parts of a silicone compound, from about 5 to 15 parts by weight of titanium dioxide, and from about 5 to 20 parts by weight of clay. The silicone-containing composition is prepared by the process of masterbatching a silicone compound, clay and titanium dioxide to form a dispersion, adding the dispersion to the elastomeric compound with stirring and thereafter forming and curing a desired product therefrom. Surgical and medical products such as Foley catheters can be formed from the silicone-containing elastomeric composition of the present invention via conventional processing techniques for natural and synthetic rubber.

PREFERRED MODE FOR CARRYING OUT THE INVENTION

Formation of the silicone-containing elastomeric composition set forth herein generally includes the use of natural rubber latex and a silicone emulsion. Although the examples provided herein disclose the use of a natural rubber latex having 56.5% total solids content by weight, it is to be understood that other latexes as well as synthetics and mixtures of the two which have conventionally been employed in the manufacture of rubber surgical and medical instruments can also be employed.

With respect to the silicone compound, one can select polysiloxanes having a viscosity of about 100 centistokes and a viscosity-average molecular weight of about 7,000, with dimethylpolysiloxane being exemplary. One particularly satisfactory silicone compound is produced by the Silicone Products Department of General Electric, and is identified by the code SM-2064. This compound is an anionic emulsion having approximately 50% total solids by weight. It requires a temperature in excess of 260° C. to increase its molecular weight and therefore, in curing operations of the type conventionally employed in the manufacture of rubber surgical and medical instruments, it retains its low molecular weight of about 7000.

The amount of the silicone compound added can range from at least 10 parts to about 50 parts by weight per hundred parts of rubber (phr). Although the silicone content is significantly higher than has been demonstrated to be practical heretofore, according to the process described herein, it is homogeneously dispersed throughout the latex composition and therefore has a greater tendency than previous compositions to remain so both during and subsequent to vulcanization. Thus, bleeding or migration of the silicone, commonly referred to as phasing and characteristic of the prior art latex-silicone mixtures, has been reduced by the present invention, allowing much higher amounts of silicone incorporation in the rubber latex without eventual separation. It is to be understood that while some controlled migration can be advantageous, the rate of migration as well as the amount must not be so great that separation or settling of the silicone from the elastomer will occur.

In addition to the conventionally employed antioxidants, pigments, curing ingredients and stabilizers which are incorporated with rubber latex compositions, practice of the present invention requires the presence of clay and titanium dioxide. The clay is added as an aqueous dispersion having about 60% total solids by weight. Kaolin is quite suitable for this purpose and can be added in amounts of from about 5 to about 20 parts by weight phr with 15 parts being preferred. Titanium dioxide is also added as an aqueous dispersion, having about 50% total solids content, in an amount of from about 5 to about 15 parts phr with 5 being preferred.

Not only must the clay and titanium dioxide be present in the composition, in order to add the relatively high amounts of silicone disclosed herein and form a homogeneous, essentially non-separating product, it is necessary to masterbatch the clay, titanium dioxide and silicone emulsion together prior to their addition to the rubber latex. If added separately, migration and eventual separation of the silicone from the latex will occur. In practice, the titanium dioxide and kaolin dispersions are combined with high speed stirring followed by the addition of the silicone emulsion at lower speeds for approximately 10 minutes. The resulting masterbatch comprises from about 20 to about 85 parts by weight of the composition, based upon the weight of the elastomer, and is added to the rubber latex base formulation utilizing conventional procedures at slow stirring speeds.

In the four examples which follow, 15, 20, 35 and 50 parts phr of silicone respectively, were masterbatched with clay and titanium dioxide, as presented in Table I, and then added to a latex rubber formulation which is given in Table II. Products were subsequently made by a conventional dipping process, vulcanized and tested with the testing results appearing in Table III. All parts are expressed in parts by weight phr and may, therefore, alternatively be considered as percent by weight, based upon the weight of the elastomer.

Although physical properties for pure gum catheters are greater than those reported hereinbelow, corresponding physical properties for an all silicone rubber are generally less. While the pure gum possesses significantly greater strength than necessary, the all silicone rubber is on the weak side for medical and surgical products. As will be readily determined from the data in Table III, the silicone-containing elastomeric compositions of the present invention have acceptable properties for medical and surgical products which are conventionally manufactured from rubber latex. Finished articles produced from this compound, multi-layered or single dip, have been found to have large amounts of silicone distributed homogeneously throughout. No phasing or separation of the silicone from the rubber latex compound, either during storage or processing, has been observed.

TABLE I

| Example Nos. | 1 | 2 | 3 | 4 |
| --- | --- | --- | --- | --- |
| TiO$_2$ | 5.0 | 5.0 | 5.0 | 5.0 |
| Percent Total Solids | 50.0% | 50.0% | 50.0% | 50.0% |
| Dry Wt. | 99.91 gms | 99.91 gms | 99.91 gms | 99.91 gms |
| Wet Wt. | 199.8 gms | 199.8 gms | 199.8 gms | 199.8 gms |
| Clay | 10.0 | 15.0 | 20.0 | 25.0 |
| Percent Total Solids | 60.0% | 60.0% | 60.0% | 60.0% |
| Dry Wt. | 199.81 gms | 299.72 gms | 399.63 gms | 499.53 gms |
| Wet Wt. | 333.0 gms | 499.5 gms | 666.0 gms | 832.5 gms |
| G.E. Silicone SM-2064 | 15.0 | 20.0 | 35.0 | 50.0 |
| Percent Total Solids | 50.0% | 50.0% | 50.0% | 50.0% |
| Dry Wt. | 299.72 gms | 399.63 gms | 699.35 gms | 999.08 gms |
| Wet Wt. | 599.48 gms | 799.3 gms | 1398.78 gms | 1998.25 gms |

TABLE II

| Component | Parts | Percent Total Solids | C.F. | Dry Wt. | Wet Wt. |
|---|---|---|---|---|---|
| Rubber latex[a] | 100.0 | 56.5% | 1.027 | 1998.13 gms | 3632.0 gms |
| Zetax[b] | 0.2 | 25.0% | | 5.99 gms | 24.0 gms |
| Methyl tuads[c] | 0.3 | 35.0% | | 5.99 gms | 17.1 gms |
| ZnO | 0.4 | 50.0% | | 7.99 gms | 16.0 gms |

[a] Natural rubber latex, contains 0.7 parts sulphur.
[b] Registered trademark of Goodyear Tire and Rubber Company for zinc 2-mercaptobenzothiazole.
[c] Registered trademark of R. T. Vanderbilt Co., Inc. for tetramethylthiuram disulfide.

TABLE III

| Example No. | Condition | Gauge | 600% Modulus (psi) | 600% Modulus (Kg/cm$^2$) | Tensile Strength (psi) | Tensile Strength (Kg/cm$^2$) | Elongation |
|---|---|---|---|---|---|---|---|
| 1 | Unaged | 0.018 ½ | 920 | 64.68 | 2780[b] | 195.45[b] | 815[b] |
| | Aged[a] | 0.019 ½ | 1080 | 75.93 | 2790 | 196.16 | 770 |
| 2 | Unaged | 0.018 ¾ | 910 | 63.98 | 2020 | 142.02 | 775[b] |
| | Aged[a] | 0.017 ¾ | 1040 | 73.12 | 2280 | 160.30 | 730 |
| 3 | Unaged | 0.020 ½ | 780 | 54.84 | 1390 | 97.73 | 730 |
| | Aged[a] | 0.018 ½ | 890 | 62.57 | 1410 | 99.13 | 690 |
| 4 | Unaged | 0.018 ½ | 610 | 42.89 | 990 | 69.60 | 700 |
| | Aged[a] | 0.020 | 310 | 21.8 | 690 | 48.51 | 660[b] |

[a] Specimens air oven aged for 168 hours at 70° C.
[b] Average value

The compositions disclosed herein are particularly suitable for the manufacture of Foley catheters made by a standard multiple dip process to build wall thickness around the drainage lumen and to form the inflatable balloon. Because the silicone compound can be considered to be essentially non-separable from the rubber latex, adhesion between successive layers is not hindered as is experienced when large amounts of silicone migrate to the exterior of a layer. Foley catheters made from the elastomeric composition disclosed herein have been tested in patients for indwelling periods of time of up to seven weeks without irritation to the patient or physical malfunction or deterioration of the catheter. In other tests, the inflation balloons of catheters have been filled with water and allowed to rest on a table for seven weeks. During this time no leakage of water was observed. Significance of the water inflation test is in the fact that all silicone catheters are permeable to water.

Thus, it can be seen that by employing the process disclosed herein, it is possible to prepare a novel elastomer having from about 10 to about 50 parts phr of a silicone compound which remains homogeneously distributed throughout the rubber latex even after vulcanization. As will be apparent to those skilled in the art, the composition of the novel elastomer disclosed herein can be selected according to availability of ingredients, desirability of process and nature of the end product. The methods generally available for making known surgical and medical instruments can be practiced with the elastomer disclosed herein which in turn can enable the worker to achieve the objects of the invention.

It is, therefore, believed that the preparation and use of silicone-containing elastomers disclosed herein can be determined without departing from the spirit of the invention herein disclosed and described, the scope of the invention being limited solely by the scope of the attached claims.

I claim:

1. Medical and surgical instruments prepared from a composition comprising:
    a natural rubber latex; and
    from about 20 to about 85 parts by weight, based upon the weight of the rubber in said latex, of a masterbatch consisting of
    a dimethylpolysiloxane compound having a viscosity average molecular weight of about 7,000 and a viscosity of about 100 centistokes, said compound being present in an amount of more than 10 to about 50 parts by weight, based upon the weight of the rubber in said latex, and being substantially free from phasing;
    from about 5 to 15 parts by weight of titanium dioxide, based upon the weight of the rubber in said latex; and,
    from about 5 to 20 parts by weight of clay, based upon the weight of the rubber in said latex.

2. Medical and surgical instruments, as set forth in claim 1, containing 15 parts by weight of said dimethylpolysiloxane compound and having a tensile strength of at least 2790 psi (196.2 Kg/cm$^2$) at 770% elongation and a 600% modulus of at least 1080 psi (75.9 Kg/cm$^2$) after aging for one week at 70° C.

3. Medical and surgical instruments, as set forth in claim 1, containing 20 parts by weight of said dimethylpolysiloxane compound and having a tensile strength of at least 2280 psi (160.3 Kg/cm$^2$) at 730% elongation and a 600% modulus of at least 1040 psi (73.1 Kg/cm$^2$) after aging for one week at 70° C.

4. Medical and surgical instruments, as set forth in claim 1, containing 35 parts by weight of said dimethylpolysiloxane compound and having a tensile strength of at least 1410 psi (99.1) Kg/cm$^2$) at 690% elongation and a 600% modulus of at least 890 psi (62.6 Kg/cm$^2$) after aging for one week at 70° C.

5. Medical and surgical instruments, as set forth in claim 1, containing 50 parts by weight of said dimethylpolysiloxane compound and having a tensile strength of at least 690 psi (48.5) Kg/cm$^2$) at 660% elongation and a 600% modulus of at least 310 psi (21.8) Kg/cm$^2$ after aging for one week at 70° C.

* * * * *